United States Patent
Schreiber et al.

(10) Patent No.: US 12,016,771 B2
(45) Date of Patent: Jun. 25, 2024

(54) INTRAOCULAR LENS

(71) Applicant: Carl Zeiss Meditec AG, Jena (DE)

(72) Inventors: Benjamin Schreiber, Berlin (DE); Thorben Badur, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/124,425

(22) Filed: Mar. 21, 2023

(65) Prior Publication Data
US 2023/0225855 A1 Jul. 20, 2023

Related U.S. Application Data

(63) Continuation of application No. PCT/US2020/051828, filed on Sep. 21, 2020.

(51) Int. Cl.
*A61F 2/16* (2006.01)

(52) U.S. Cl.
CPC .......... *A61F 2/1613* (2013.01); *A61F 2/1632* (2013.01); *A61F 2002/1682* (2015.04); *A61F 2002/16903* (2015.04)

(58) Field of Classification Search
CPC .......... A61F 2/1632; A61F 2002/16903; A61F 2002/1682
See application file for complete search history.

(56) References Cited

U.S. PATENT DOCUMENTS

| | | | | |
|---|---|---|---|---|
| 5,571,177 A * | 11/1996 | Deacon | ................. | A61F 2/1613 623/6.47 |
| 2003/0171809 A1* | 9/2003 | Phillips | ................. | A61F 2/1629 623/6.46 |
| 2014/0200666 A1* | 7/2014 | Phillips | ............... | A61F 9/00827 623/6.46 |
| 2016/0030163 A1* | 2/2016 | Akahoshi | .............. | A61F 2/1694 623/6.12 |
| 2018/0338827 A1 | 11/2018 | Goldshleger et al. | | |
| 2019/0125523 A1* | 5/2019 | Barzilay | .............. | H10N 30/857 |
| 2021/0177581 A1* | 6/2021 | Bensaid | ................ | A61F 2/1645 |

OTHER PUBLICATIONS

Written Opinion and International Search Report dated Jun. 24, 2021 of international application PCT/US2020/051828 on which this application is based.
Clayden at al., Organic Chemistry, 2001, p. 906-p. 942, published in the United States by Oxford University Press Inc., New York.

* cited by examiner

*Primary Examiner* — Javier G Blanco
(74) *Attorney, Agent, or Firm* — Ewers IP Law PLLC; Falk Ewers (57) ABSTRACT

An intraocular lens has an optic body, a haptic element mounted on the optic body and having a haptic curvature and a plurality of recesses on the side of the haptic element facing the optic body, a first actuator configured to reversibly change the haptic curvature of the haptic element such that the haptic element is moved away from the optic body from a rest position, a brace arm mounted on the optic body and the longitudinal brace arm end which is configured to be provided a recess when the haptic element is in the rest position, and a second actuator configured to reversibly change, with a change in a property of the second actuator, a brace arm curvature of the brace arm such that the recess in which the longitudinal brace arm end is to be provided can be adjusted with the property of the second actuator.

14 Claims, 3 Drawing Sheets

INTRAOCULAR LENS

CROSS REFERENCE TO RELATED APPLICATIONS

This application is a continuation application of international patent application PCT/US2020/051828, filed Sep. 21, 2020, designating the United States, and the entire content of this application is incorporated herein by reference.

TECHNICAL FIELD

The disclosure relates to an intraocular lens.

BACKGROUND

In cataract treatment of an eye, an incision is conventionally made in the cornea of the eye, said incision being large enough to allow a cannula to be inserted through the incision into the eye. After the incision has been made in the cornea, the lens of the eye is broken up by phacoemulsification and then sucked out of the capsular bag of the eye. Thereafter, an intraocular lens is inserted into the capsular bag with an injector. The intraocular lens includes an optic body and a haptic element, wherein the haptic element fixes the optic body in the capsular bag.

The haptic element has the function of keeping the optic body as close as possible to the middle of the eye in order to generate an image of maximum quality on the retina of the eye. Moreover, the optic body should be fixed with maximum positional stability in the capsular bag. In addition, the haptic element has the function of stopping the optic body from rotating about its optical axis. This is particularly relevant when the optic body is a toric optic body with which cornea curvature is to be corrected, because the toric optic body, if it is arranged in the capsular bag with an incorrect orientation, leads to an imaging aberration on the retina.

Once the intraocular lens has been inserted into the capsular bag, the intraocular lens may be disposed in an incorrect position in the capsular bag. This may be caused, for example, by nonuniform fibrosis. If the intraocular lens has been disposed in the wrong position in the capsular bag, it is necessary to correct the position of the intraocular lens in a surgical intervention or even to change the intraocular lens. Remedy could be provided by an intraocular lens having a correctable position after the insertion of the intraocular lens.

SUMMARY

It is therefore an object of the disclosure to provide an intraocular lens having a correctable position after it has been inserted into a capsular bag of an eye.

The intraocular lens according to an aspect of the disclosure has an optic body, a haptic element which has been mounted on the optic body and has a haptic curvature and has a plurality of recesses on the side of the haptic element facing the optic body, a first actuator set up to reversibly change, with a change in a property of the first actuator, the haptic curvature of the haptic element in such a way that the haptic element is moved away from the optic body from a rest position of the haptic element, a brace arm which has been mounted on the optic body and the longitudinal brace arm end of which, remote from the optic body, has been set up to be disposed in one of the recesses when the haptic element is in the rest position of the haptic element, and a second actuator set up to reversibly change, with a change in a property of the second actuator, a brace arm curvature of the brace arm such that the recess in which the longitudinal brace arm end is to be disposed can be adjusted with the property of the second actuator.

When the intraocular lens has been inserted into a capsular bag of an eye and the haptic element is in its rest position, the longitudinal brace arm end is disposed in an original recess of the recesses. It is then possible to change the property of the first actuator in that the first actuator is irradiated with electromagnetic radiation, for example with a laser. As a result, the haptic element moves away from the optic body from its rest position and the longitudinal brace arm end leaves the original recess. It is then possible to irradiate the second actuator with electromagnetic radiation, for example with a laser. In this way, it is possible to alter the property of the second actuator, which changes the brace arm curvature. According to the significance of the change in the property of the second actuator, it is then possible to choose which of the recesses the longitudinal brace arm end is disposed in when the first actuator has moved back in the direction of the initial position into a new rest position. It is conceivable here that the longitudinal brace arm end is disposed in one of the recesses other than the original recess. By virtue of the choice of which of the recesses the longitudinal brace arm end is now disposed in, the haptic element assumes a different position relative to the optic body. In this way, it is possible to change the position of the optic body in the capsular bag. Because all that is required for this purpose is to irradiate the first actuator and the second actuator with the electromagnetic radiation, it is advantageously unnecessary to introduce a surgical instrument into the capsular bag via the cornea of the eye.

The property of the first actuator may, for example, be the temperature of the first actuator and/or the phase of the first actuator. The property of the second actuator may, for example, be the temperature of the second actuator and/or the phase of the second actuator. The phase is understood to mean a spatial region in which the material properties are homogeneous. A change in the phase is understood to mean, for example, a transition from solid to liquid or from liquid to solid, or a transition from liquid to gaseous or from gaseous to liquid. A chemical transformation, for example from a monomer to a dimer or from a dimer to a monomer, also constitutes a change in phase.

It is typical that the property of the first actuator is the temperature of the first actuator and the first actuator includes a bimetal of the first actuator that extends within the haptic element, and/or wherein the property of the second actuator is the temperature of the second actuator and the second actuator includes a bimetal of the second actuator that extends within the brace arm. The bimetal may be formed, for example, by stainless steel and zinc. Stainless steel has a coefficient of thermal expansion of $12*10{-6}/K$, and zinc has a coefficient of thermal expansion of $30*10{-6}/K$. These coefficients of thermal expansion are significantly different from one another, such that long movements of the haptic element and/or the brace arm can be achieved even with small changes in temperature with stainless steel and zinc.

The haptic element is typically in the rest position of the haptic element when the temperature of the first actuator is below a threshold temperature of the first actuator and is set up to move away from the optic body when the first actuator is heated to temperatures above the threshold temperature of the first actuator. The threshold temperature of the first actuator may be chosen such that it is just above body temperature, for example higher than 40° C. More particularly, the threshold temperature of the second actuator may be from 40° C. to 50° C. As a result, the haptic element automatically moves back to its rest position when the haptic element cools down to body temperature through conduction of heat.

The first actuator typically has a thickening of the first actuator, said thickening having thermally conductive bonding to the bimetal of the first actuator, and/or the second actuator typically has a thickening of the second actuator, said thickening having thermally conductive bonding to the bimetal of the second actuator. It is advantageously simple for the laser to focus on and irradiate the thickening. The thickening of the first actuator and/or the thickening of the second actuator are more typically disposed in the region of the optic body. This region is not normally disposed behind the iris of the eye but rather centrally in the capsular bag and can therefore be reached easily by the electromagnetic radiation. Alternatively, the thickening of the first actuator and/or the thickening of the second actuator are disposed in a region of the periphery of the optic body. This region may be disposed close to the optic body. More typically, the thickening of the first actuator and/or the thickening of the second actuator are disposed in a region adjoining the optic body. These alternatives enable the positioning of the thickening behind the iris of the eye and hence outside the field of view of a patient. A change in the property or an activation of the first actuator and/or the second actuator can be effected with electromagnetic radiation. This is typically effected after preceding medicament-induced dilation of the pupil.

It is typical that the first actuator includes a reservoir of the first actuator and a conduit of the first actuator that extends within the haptic element, wherein a substance of the first actuator is disposed in the reservoir of the first actuator and in the conduit of the first actuator, wherein the reservoir of the first actuator and the conduit of the first actuator are connected to one another in a fluid-conducting manner and the property of the first actuator is the temperature of the substance of the first actuator and/or the phase of the substance of the first actuator. It is typical that the second actuator includes a reservoir of the second actuator and a conduit of the second actuator that extends within the brace arm, wherein a substance of the second actuator is disposed in the reservoir of the second actuator and in the conduit of the second actuator, wherein the reservoir of the second actuator and the conduit of the second actuator are connected to one another in a fluid-conducting manner and the property of the second actuator is the temperature of the substance of the second actuator and/or the phase of the substance of the second actuator. A change in the temperature of the substance and/or the phase of the substance changes the pressure within the reservoir and the conduit. The change in the pressure can reversibly alter the haptic element curvature or the brace arm curvature. The provision of the reservoir results in a more significant rise in the pressure by comparison with lack of provision of the reservoir. Moreover, it is particularly easy for the laser to focus on the reservoir and hence to irradiate a large amount of the substance. The change in the pressure is particularly high when the reservoir and the conduit are completely filled with the substance.

The substance is typically gaseous and/or liquid. The liquid and/or gaseous substance is particularly suitable when the property of the first actuator and/or the second actuator is the temperature of the substance because flowing of the substance from the reservoir into the conduit and vice versa can effectively change the pressure in the conduit.

The substance typically has a photosystem including an amount of a monomer and/or an amount of a dimer, wherein two of the monomers are set up to enter into a photoaddition with one another, especially a photocycloaddition, especially a [2+2] photocycloaddition, and hence to form the dimer, and the dimer is set up to enter into a photodissociation and hence to form two of the monomers. Such reactions are known to the person skilled in the art (see, for example, Jonathan Clayden, Nick Geeves, Stuart Warren, Organic Chemistry, Oxford University Press, 2006). For example, the photosystem for this purpose may include coumarin, a coumarin derivative, a cinnamic ester, especially methyl cinnamate, a cinnamic ester derivative, or a stilbene derivative, and/or the dimer of the aforementioned compounds. One example of photoaddition and photodissociation is depicted in reaction equation (1) below for coumarin or the coumarin derivative, with the dimer depicted on the right of the reaction arrow and the monomer on the left of the reaction arrow:

(1)

R may be, for example, —H, —NR'2, —NH2, —NH-COR', —OH or —OR', where the substance is coumarin when R=—H. R' may be an aliphatic or aromatic radical or an acrylate. Irradiation with a wavelength $\lambda_2$ leads to formation of the dimer; irradiation with a wavelength $\lambda_1$ leads to dissociation of the dimer into the monomer. The dimer has a higher density than the monomer. Irradiation with the wavelength $\lambda_2$ thus leads to lowering of the pressure in the conduit; irradiation with the wavelength $\lambda_1$ leads to an increase in the pressure in the conduit.

A further example of photoaddition and photodissociation is depicted in reaction equation (2) below for methyl cinnamate, with the dimer depicted on the right of the reaction arrow and the monomer on the left of the reaction arrow:

(2)

-continued

Irradiation with a wavelength λ2 leads to formation of the dimer; irradiation with a wavelength λ1 leads to dissociation of the dimer into the monomer. The dimer has a higher density than the monomer. Irradiation with the wavelength λ2 thus leads to lowering of the pressure in the conduit; irradiation with the wavelength λ1 leads to an increase in the pressure in the conduit.

A further example of photoaddition and photodissociation is depicted in reaction equation (3) below for a stilbene derivative, with the dimer depicted on the right of the reaction arrow and the monomer on the left of the reaction arrow:

(3)

-continued

The dimer is present in two isomers. Irradiation with a wavelength λ2 leads to formation of the dimer; irradiation with a wavelength λ1 leads to dissociation of the dimer into the monomer. The dimer has a higher density than the monomer. Irradiation with the wavelength λ2 thus leads to lowering of the pressure in the conduit; irradiation with the wavelength λ1 leads to an increase in the pressure in the conduit.

If the wavelength λ1 and/or the wavelength λ2 is in the ultraviolet range, it is conceivable to irradiate the first actuator and/or the second actuator with light pulses of short duration of a wavelength λ1/n and/or a wavelength λ2/n in order that multiphoton absorption with n photons can take place.

The intraocular lens typically includes a bandpass filter that has been disposed around the substance and is set up to allow a first wavelength range and a second wavelength range to pass through to the photosystem, wherein an irradiation of the photosystem in the first wavelength range leads to dissociation of the dimer and an irradiation of the photosystem in the second wavelength range leads to formation of the dimer. In this way, it is possible to prevent an unwanted phase transition of the substance resulting from incidence of daylight into the eye. The substance may, for example, be mixed with the bandpass filter or the bandpass filter may be disposed around the substance. It is particularly typical that the first wavelength range has the wavelength λ1 and the second wavelength range has the wavelength λ2.

It is typical that the reservoir of the first actuator is disposed in the region of the optic body and/or the reservoir of the second actuator is disposed in the region of the optic body. This region is not normally disposed behind the iris of the eye but rather centrally in the capsular bag, and can therefore be reached easily by the electromagnetic radiation. Alternatively, the reservoir of the first actuator and/or the reservoir of the second actuator are disposed in a region of the periphery of the optic body. This region may be disposed close to the optic body. More typically, the reservoir of the first actuator and/or the reservoir of the second actuator are disposed in a region adjoining the optic body. These alternatives enable the positioning of the reservoir behind the iris of the eye and hence outside the field of view of a patient. A change in the property or activation of the first actuator and/or the second actuator can be effected with electromagnetic radiation. This is typically effected after preceding medicament-induced dilation of the pupil.

It is typical that the recesses are arranged alongside one another in a direction from a first longitudinal end of the haptic element to a second longitudinal end of the haptic element. It is typical here that the first longitudinal haptic element end is disposed on the optic body and the second longitudinal haptic element end is disposed remote from the optic body, or the first longitudinal haptic element end is disposed remote from the optic body and the second longitudinal haptic element end is disposed on the optic body.

It is typical that whichever of the first longitudinal haptic element end and the second longitudinal haptic element end that is disposed remote from the optic body is disposed at a different distance away from the optic body according to which of the recesses the longitudinal brace arm end is disposed in.

It is typical that the property of the second actuator is the temperature of the second actuator, wherein the longitudinal brace arm end is set up to be disposed in one of the recesses in the region of the first longitudinal haptic element end when the temperature of the second actuator is below a threshold temperature of the second actuator, and to move in the direction of the second longitudinal end when the second actuator is heated to temperatures above the threshold temperature of the second actuator. It is conceivable here that, below the threshold temperature of the second actuator, the longitudinal brace arm end is disposed in that recess disposed closest to the first longitudinal haptic element end. The threshold temperature of the second actuator may be chosen such that it is above body temperature, for example higher than 40° C. More particularly, the threshold temperature of the second actuator may be from 40° C. to 50° C. By virtue of the threshold temperature being above body temperature and the longitudinal haptic element end below the threshold temperature being disposed in that recess closest to the first longitudinal haptic element end, it is possible to achieve the effect that, when the haptic element is spaced apart from its first position, the longitudinal brace arm end can be brought into each of the recesses by heating the actuator by irradiating with the electromagnetic radiation.

There is typically a locking tooth disposed between every two adjacent recesses that has a first flank arranged to face the first longitudinal haptic element end and a second flank arranged to face the second longitudinal haptic element end, wherein the first flank and the second flank are shaped such that, when the haptic element is in its first position, sliding of the longitudinal brace arm end in the direction of the second longitudinal haptic element end is enabled and sliding of the longitudinal brace arm end toward the first longitudinal haptic element end is prevented. What can be achieved in this way is that the longitudinal brace arm end, in the event of cooling of the second actuator, does not move in the direction of the first longitudinal end. At the same time, however, in the event of heating of the second actuator, the movement of the longitudinal brace arm end in the direction toward the second longitudinal haptic element end is facilitated. In order to achieve this, for example, the first flank may protrude steeper from the surface of the haptic element than the second flank, as is the case, for example, in a sawtooth profile.

It is typical that one locking tooth is disposed between every two adjacent recesses.

It is typical that the haptic element includes a polymer that comes into contact with the first actuator, and/or wherein the brace arm includes a polymer of the brace arm that comes into contact with the second actuator. The providing of the polymer allows the haptic element to easily change its haptic curvature, and the brace arm to easily change its brace arm curvature. If the reservoir and the conduit are provided, it is typical that the polymer bounds, and especially completely bounds, the reservoir and the conduit. If the bimetal is provided, it is typical that the polymer encapsulates, and especially fully encapsulates, the bimetal. In this way, it is also possible to use non-biocompatible metals in the bimetal.

The intraocular lens typically has two of the haptic elements, one of the first actuators and one of the brace arms for each of the haptic elements, and one of the second actuators for each brace arm. As a result, it is possible to change the position of the optic body from two different directions.

BRIEF DESCRIPTION OF THE DRAWINGS

The disclosure will now be described with reference to the drawings wherein.

DESCRIPTION OF EXEMPLARY EMBODIMENTS

Figure 1:
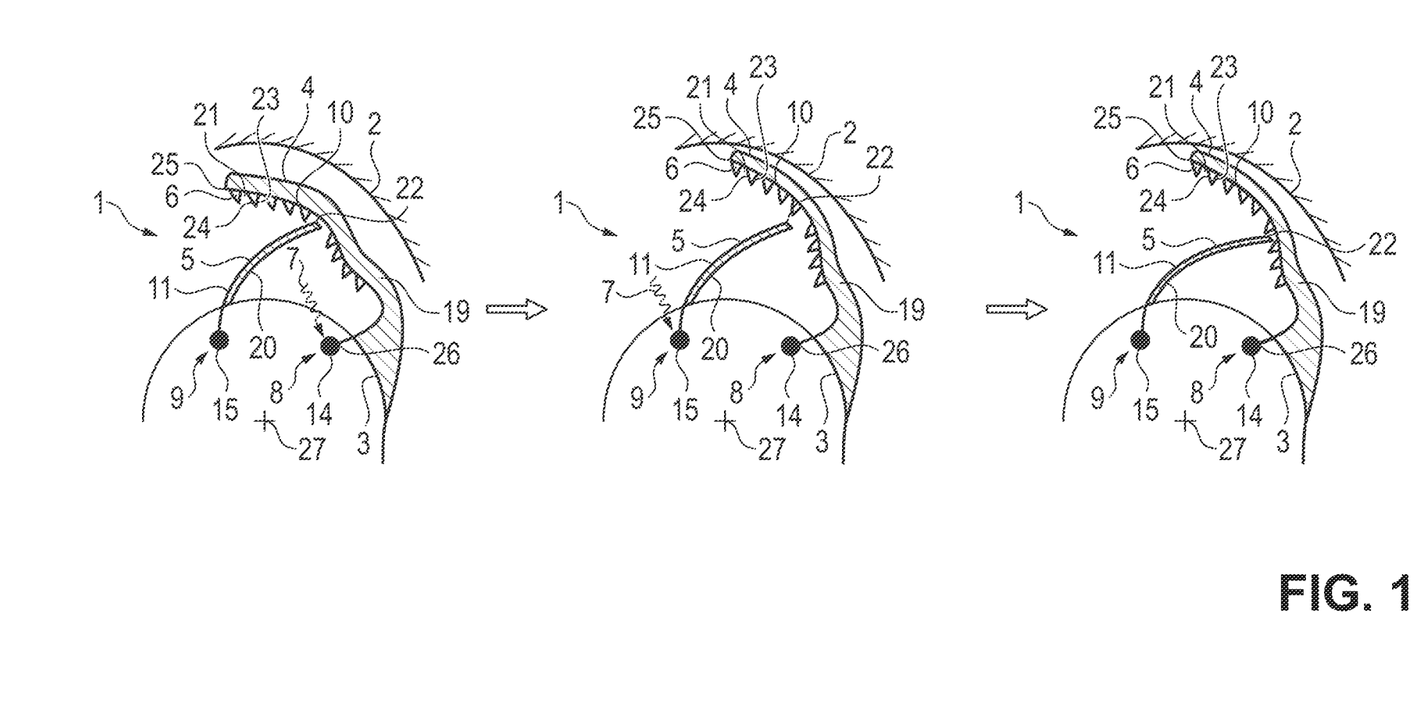
FIG. 1 shows the intraocular lens according to a first exemplary embodiment of the disclosure.

As apparent from FIG. 1, an intraocular lens 1 has an optic body 3, a haptic element 4 mounted on the optic body 3, a first actuator 8, a brace arm 5 mounted on the optic body 3, and a second actuator 9. The haptic element 4 has a haptic curvature, and a plurality of recesses 21 on the side of the haptic element 4 facing the optic body 3. The first actuator 8 is set up, with a change in a property of the first actuator 8, to reversibly alter the haptic curvature of the haptic element 4 in such a way that the haptic element 4 is moved away from the optic body 3 from a rest position of the haptic element 4. The longitudinal brace arm end 22 remote from the optic body 3 is set up to be disposed in one of the recesses 21 when the haptic element 4 is in the rest position of the haptic element 4, and the second actuator 9 is set up, with a change in a property of the second actuator 9, to reversibly alter a brace arm curvature of the brace arm 5 such that the recess 21 in which the longitudinal brace arm end 22 is to be disposed can be adjusted with the property of the second actuator 9.

FIG. 1 shows that the haptic curvature and/or the brace arm curvature may be formed in a plane having a normal arranged parallel to the optical axis 27 of the optic body 3. More particularly, it is conceivable that the haptic element 4 is in C-shaped form. It is additionally conceivable that the intraocular lens 1 has two of the haptic elements 4, one of the first actuators 8 and one of the brace arms 5 for each of the haptic elements 4, and one of the second actuators 9 for each brace arm 5.

Moreover, FIG. 1 shows that the recesses 21 may be arranged alongside one another in a direction from a first longitudinal end 25 of the haptic element 4 to a second longitudinal end 26 of the haptic element 4. As apparent from FIG. 1, the first longitudinal haptic element end 25 may be disposed remote from the optic body 3 and the second longitudinal haptic element end 26 may be disposed on the optic body 3. Alternatively, it is conceivable that the first longitudinal haptic element end 25 is disposed on the optic body 3 and the second longitudinal haptic element end 26 is disposed remote from the optic body 3. Whichever of the first longitudinal haptic element end 25 and the second longitudinal haptic element end 26 that is disposed remote from the optic body 3 may be disposed at a different distance away from the optic body 3 according to which of the recesses 21 the longitudinal brace arm end 22 is disposed in.

FIG. 1 shows how the position of the optic body 3 can be altered when the intraocular lens 1 has been introduced into the capsular bag 2 of an eye. The intraocular lens 1 and the capsular bag 2 are shown at three different junctures, with advancing time from left to right. At the first juncture, the haptic element 4 is in its rest position and the longitudinal brace arm end 22 is disposed in an original recess of the recesses 21. At the first juncture, the property of the first actuator 8 is altered by irradiating the first actuator 8 with electromagnetic radiation 7. This can be effected, for example, with a laser. At the second juncture, it is shown that this causes the haptic element 4 to move from its rest position away from the optic body 3 and toward the capsular bag 2. This extends the distance between the longitudinal brace arm end 22 and the original recess. It is additionally shown that, at the second juncture, the property of the second actuator 9 can be changed, for example by irradiating the second actuator 9 with electromagnetic radiation 7, for example with a laser. This changes the brace arm curvature. At the third juncture, it is shown that the haptic element 4 is disposed in a further rest position. Moreover, the longitudinal brace arm end 22 is now disposed closer to the optic body 3 than at the first juncture and in one of the recesses 21 other than the original recess. As a result, the haptic element 4 at the third juncture is disposed further away from the optic body 3 than at the first juncture. Alternatively, it is conceivable that the longitudinal brace arm end 22 at the third juncture is disposed further away from the optic body 3 than at the first juncture and in one of the recesses 21 other than the original recess, as a result of which the haptic element 4 at the third juncture is disposed closer to the optic body 3 than at the first juncture. In this way, it is possible to change the position of the optic body 3 in the capsular bag 2.

Figure 3:
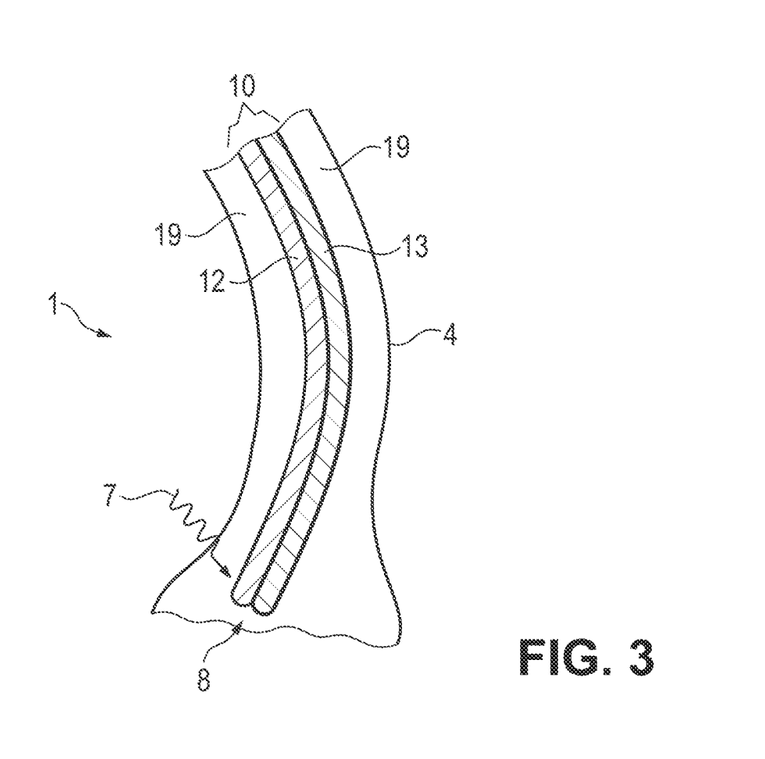
FIG. 3 shows a detail of the intraocular lens according to a third exemplary embodiment of the disclosure.
Figure 4:
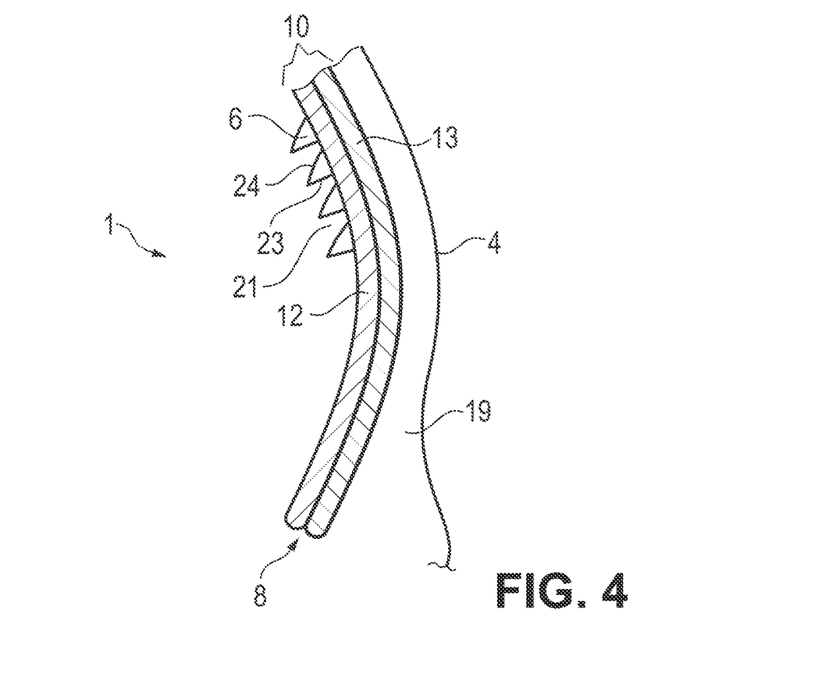
FIG. 4 shows a detail of the first exemplary embodiment.

FIGS. 1, 3, and 4 show that, in the first and third exemplary embodiments of the intraocular lens 1, the property of the first actuator 8 may be the temperature of the first actuator 8, and that the first actuator 8 may include a bimetal 10 of the first actuator 8 that extends within the haptic element 4. Moreover, the property of the second actuator 9 may be the temperature of the second actuator 9, and the second actuator 9 may include a bimetal 11 of the second actuator 9 that extends within the brace arm 5. FIGS. 3 and 4 show that the bimetal 10 of the first actuator 8 may have a first metal 12 and a second metal 13 that are in elongated form and arranged alongside one another in a direction perpendicular to the longitudinal direction of the first metal 12 and of the second metal 13, with the second metal 13 disposed further to the outside than the first metal 12 with respect to the optic body 3. It is conceivable here that the first metal 12 has a higher coefficient of thermal expansion than the second metal 13. This is the case, for example, when the first metal 12 is zinc and the second metal 13 is stainless steel. What is achieved by virtue of the first metal 12 having the higher coefficient of thermal expansion than the second metal 13 is that the haptic element 4 moves outward when the first actuator 8 is heated. It is analogously conceivable that the bimetal 11 of the second actuator 9 may have a first metal and a second metal that are in elongated form and arranged alongside one another in a direction perpendicular to the longitudinal direction of the first metal and of the second metal, where the first metal and the second metal 12 and a different coefficient of thermal expansion. The metal is also understood to mean an alloy.

As apparent from FIG. 1, the bimetal 10 of the first actuator 8 may extend into the optic body 3. Moreover, the bimetal 11 of the second actuator 9 may extend into the optic body 3.

It is conceivable that the haptic element 4 is in its rest position when the temperature of the first actuator 8 is below a threshold temperature of the first actuator 8 and is set up to move away from the optic body 3 when the first actuator 8 is heated to temperatures above the threshold temperature of the first actuator 8. The threshold temperature of the first actuator 8 may be selected such that it is just above body temperature, for example higher than 40° C. More particularly, the threshold temperature of the second actuator may be from 40° C. to 50° C. For example, what can be achieved by such a choice of the threshold temperature is that the haptic element 4, at the third juncture according to FIG. 1, moves back into its rest position as a result of cooling of the first actuator 8 through conduction of heat.

FIG. 1 shows that the first actuator 8 may have a thickening 14 of the first actuator 8 connected in a thermally conductive manner to the bimetal 10 of the first actuator 8. More particularly, the thickening 14 of the first actuator 8, in a plane having a normal arranged parallel to the optical axis 27 of the optic body 3, may be thicker than the remaining portion of the bimetal 10 of the first actuator 8. Moreover, the second actuator 9 may have a thickening 15 of the second actuator 9 connected in a thermally conductive manner to the bimetal 11 of the second actuator 9. More particularly, the thickening 15 of the second actuator 9, in a plane having a normal arranged parallel to the optical axis 27 of the optic body 3, may be thicker than the remaining portion of the bimetal 11 of the second actuator 9. Moreover, FIG. 1 shows that the thickening 14 of the first actuator 8 and/or the thickening 15 of the second actuator 9 may be disposed in the region of the optic body 3.

Figure 2:
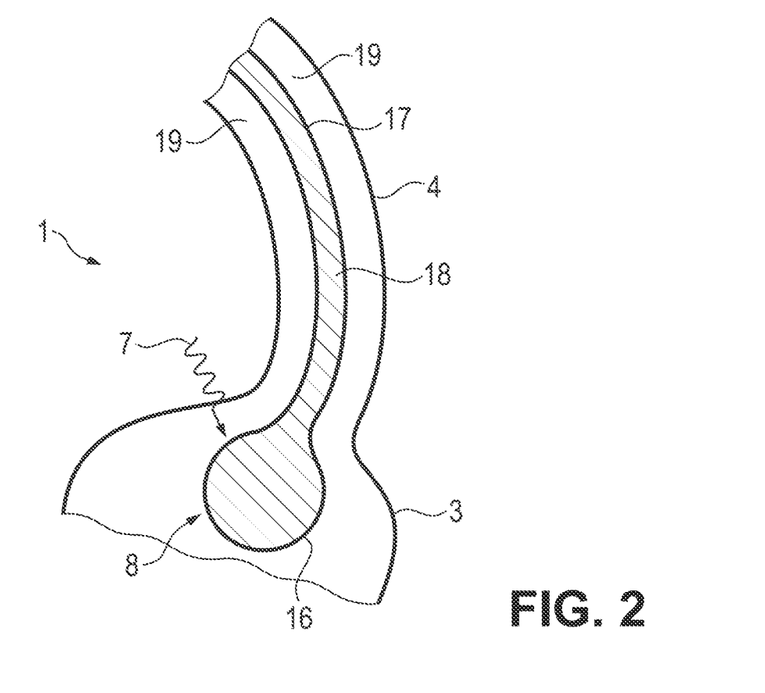
FIG. 2 shows a detail of the intraocular lens according to a second exemplary embodiment of the disclosure.

FIG. 2 shows that, in the second embodiment of the intraocular lens 1, the first actuator 8 may have a reservoir 16 of the first actuator 8 and a conduit 17 of the second actuator 8 that extends within the haptic element 4. A substance 18 of the first actuator 8 may be disposed in the reservoir 16 of the first actuator 8 and in the conduit 17 of the first actuator 8. The reservoir 16 of the first actuator 8 and the conduit 17 of the first actuator 8 may be connected to one another in a fluid-conducting manner. The property of the first actuator 8 may be the temperature of the substance 18 of the first actuator 8 and/or the phase of the substance 18 of the first actuator 8. It is conceivable here that the reservoir 16 of the first actuator 8 and the conduit 17 of the first actuator 8 are completely filled with the substance 18 of the first actuator 8. It is also conceivable that the second actuator 9 may have a reservoir of the second actuator 9 and a conduit of the second actuator 9 that extends within the brace arm 5, wherein a substance of the second actuator 9 is disposed in the reservoir of the second actuator 9 and in the conduit of the second actuator 9. The reservoir of the second actuator 9 and the conduit of the second actuator 9 may be connected to one another in a fluid-conducting manner. The property of the second actuator 9 may be the temperature of the substance of the second actuator 9 and/or the phase of the substance of the second actuator 9. It is conceivable here that the reservoir of the second actuator 9 and the conduit of the second actuator 9 are completely filled with the substance of the second actuator 9. The phase is understood to mean a spatial region in which the material properties are homogeneous. A change in the phase is understood to mean, for example, a transition from solid to liquid or from liquid to solid, or a transition from liquid to gaseous or from gaseous to liquid. A chemical transformation, for example from a monomer to a dimer or from a dimer to a monomer, also constitutes a change in phase.

FIG. 2 shows that, in a plane having a normal parallel to the optical axis 27 of the optic body 3, the reservoir 16 of the first actuator 8 may be broader than the conduit 17 of the first actuator 8. It is additionally conceivable that, in a plane having a normal parallel to the optical axis 27 of the optic body 3, the reservoir of the second actuator 9 may be broader than the conduit of the second actuator 9. FIG. 2 additionally shows that the reservoir 16 of the first actuator 8 may be disposed in the region of the optic body 3. It is also conceivable that the reservoir of the second actuator 9 may be disposed in the region of the optic body 3.

For example, the substance 18 of the first actuator 8 may be gaseous and/or liquid. For example, the substance of the second actuator 9 may be gaseous and/or liquid.

It is conceivable that the substance 18 has a photosystem including an amount of a monomer and/or an amount of a dimer, wherein two of the monomers are set up to enter into a photoaddition with one another, especially a photocycloaddition, especially a [2+2] photocycloaddition, and hence to form the dimer, and the dimer is set up to enter into a photodissociation and hence to form two of the monomers. For example, the photosystem for this purpose may include coumarin, a coumarin derivative, a cinnamic ester, especially methyl cinnamate, a cinnamic ester derivative, or a stilbene derivative, and/or the dimer of the aforementioned compounds.

In order to prevent unwanted formation of the dimer or unwanted breakdown of the dimer, the intraocular lens 1 may include a bandpass filter that has been disposed around the substance 18 and is set up to allow a first wavelength range $\Lambda_1$ and a second wavelength range $\Lambda_2$ to pass through to the photosystem, wherein an irradiation of the photosystem in the first wavelength range $\Lambda_1$ leads to dissociation of the dimer and an irradiation of the photosystem in the second wavelength range $\Lambda_2$ leads to formation of the dimer. The substance may, for example, be mixed with the bandpass filter or the bandpass filter may be disposed outside the conduit and/or the reservoir.

Figure 5:
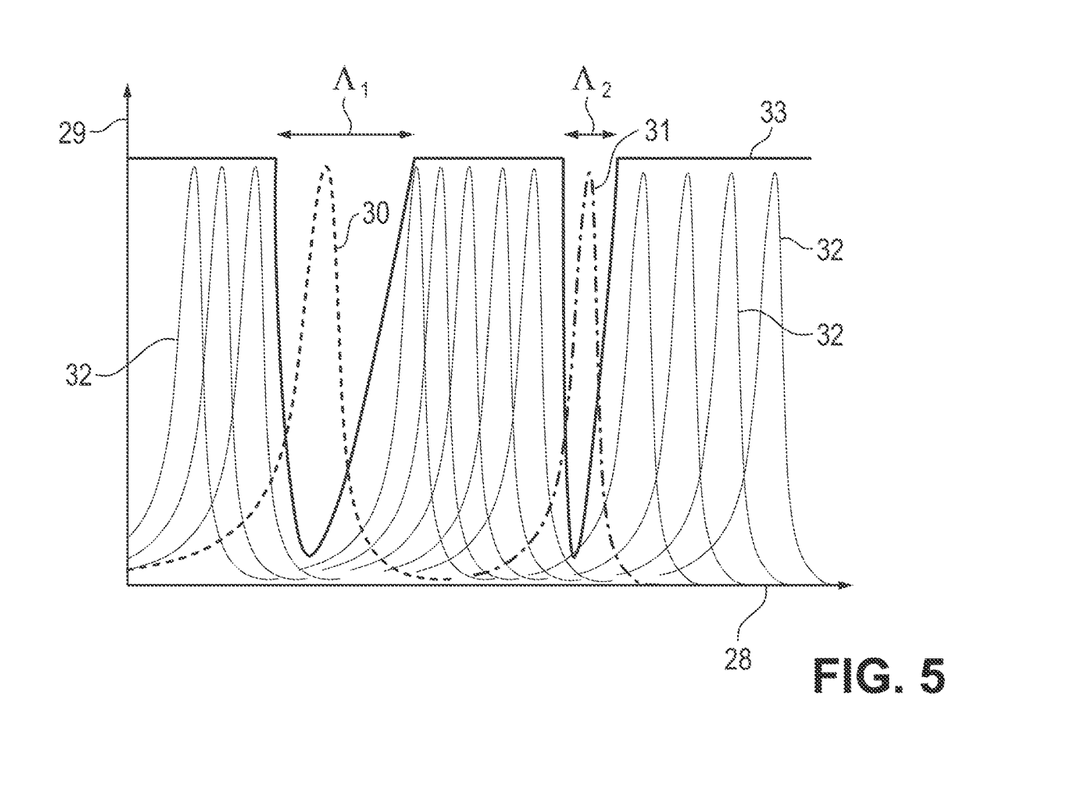
FIG. 5 shows an absorption spectrum of a bandpass filter.

FIG. 5 shows an example of the absorption spectrum of the bandpass filter. The wavelength 28 is plotted across the abscissa, and the absorption 29 is plotted across the ordinate. The bandpass filter has a plurality of different absorbers that each have an individual absorption band 32. All the individual absorption bands 32 cumulatively result in an overall absorption 33 of the bandpass filter. The overall absorption 33 is smaller in the first wavelength range $\Lambda_1$ and in the second wavelength range $\Lambda_2$ than in the adjacent wavelength ranges. The absorption band 30 of the dimer is disposed in the first wavelength range $\Lambda_1$, and the absorption band 31 of the monomer is disposed in the second wavelength range $\Lambda_2$. FIG. 5 shows that the first wavelength range $\Lambda_1$ and the second wavelength range $\Lambda_2$ are separated from one another. It is alternatively conceivable that the first wavelength range $\Lambda_1$ and the second wavelength range $\Lambda_2$ overlap one another.

FIG. 1 shows that the property of the second actuator 9 may be the temperature of the second actuator 9, wherein the longitudinal brace arm end 22 is set up to be disposed in one of the recesses 21 in the region of the first longitudinal haptic element end 25 when the temperature of the second actuator 9 is below a threshold temperature of the second actuator 9, and to move in the direction of the second longitudinal end 26 when the second actuator 9 is heated to temperatures above the threshold temperature of the second actuator 9. The threshold temperature of the second actuator 9 may be chosen such that it is just above body temperature, for example higher than 40° C. More particularly, the threshold temperature of the second actuator 9 may be from 40° C. to 50° C. For example, such a choice of threshold temperature can achieve the effect that the longitudinal brace arm end 22, in the event of cooling, through conduction of heat, is moved automatically in the direction of the first longitudinal haptic element end 22.

It is additionally apparent from FIG. 1 that a locking tooth 6 may be disposed between every two adjacent recesses 21 and has a first flank 23 arranged to face the second longitudinal haptic element end 26 and a second flank 24 arranged to face the first longitudinal haptic element end 25, wherein the first flank 23 and the second flank 24 are shaped such that, when the haptic element 4 is in its rest position, sliding of the longitudinal brace arm end 22 in the direction of the second longitudinal haptic element end 26 is enabled and sliding of the longitudinal brace arm end 22 toward the first longitudinal haptic element end 25 is prevented. As a result, the movement of the longitudinal brace arm end 22 is facilitated in the event of heating of the second actuator 9. By contrast, in the event of cooling of the second actuator 9, the movement of the longitudinal brace arm end is prevented when the haptic element 4 is in its rest position. This behavior of the longitudinal brace arm end 22 can be achieved, for example, in that the first flank 23 protrudes steeper than the second flank 24 from the surface of the haptic element 4.

FIGS. 1 to 4 show that the haptic element 4 may include a polymer 19 that makes contact with the first actuator 8. It is conceivable here that the polymer 19 is identical to the material of the optic body 3. For example, the polymer 19 of the haptic element 4 may be a silicone and/or a polyacrylate. The glass transition temperature of the polymer 19 of the haptic element 4 may, for example, be below body temperature, i.e., for example, lower than 37° C. As a result, the polymer 19 of the haptic element 4 is soft when it is disposed in the capsular bag 2, and hence deformable. Alternatively, it is conceivable that the glass transition temperature of the polymer 19 of the haptic element 4 is above body temperature; more particularly, the glass transition temperature is from 37° C. to 41° C. This makes it possible to soften the polymer 19 of the haptic element 4 in that the first actuator 8 is heated and, as a result of conduction of heat proceeding from the first actuator 8, the polymer of the haptic element 4 is heated to temperatures above the glass transition temperature. The glass transition temperature is the temperature at which the polymer undergoes a phase transition from a solid state to a viscous state. The glass transition temperature can be determined at the temperature at which the viscous state of the polymer begins to form. In the first embodiment of the intraocular lens 1 according to FIGS. 1 and 4, the polymer 19 of the haptic element 4 makes contact with the first actuator 8 on that side of the actuator 8 disposed remote from the optic body 3. The side of the first actuator 8 disposed facing the optic body 3 is free of the polymer 19 of the haptic element 4. Instead, the locking teeth 6 may be mounted on the side of the first actuator 8 disposed facing the optic body 3. In the second embodiment of the intraocular lens 1 according to FIG. 2, the polymer 19 of the haptic element 4 completely ensheaths the conduit 17 of the first actuator 8 that extends within the haptic element 4. In the third embodiment of the intraocular lens 1 according to FIG. 3, the polymer 19 of the haptic element 4 completely ensheaths the bimetal 10 of the first actuator 8 that extends within the haptic element 4.

As apparent from FIG. 1, the brace arm 5 may include a polymer 20 that forms contact with the second actuator 9. It is conceivable here that the polymer 19 of the haptic element 4 is identical to the material of the optic body 3. For example, the polymer 20 of the brace arm 5 may be a silicone and/or a polyacrylate. The glass transition temperature of the polymer 20 of the brace arm 5 may, for example, be below body temperature, i.e., for example, lower than 37° C. As a result, the polymer 20 of the brace arm 5 is soft when it is disposed in the capsular bag 2, and hence deformable. Alternatively, it is conceivable that the glass transition temperature of the polymer 20 of the brace arm 5 is above body temperature; more particularly, the glass transition temperature is from 37° C. to 41° C. This makes it possible to soften the polymer 20 of the brace arm in that the second actuator 9 is heated and, as a result of conduction of heat proceeding from the second actuator 9, the polymer 20 of the brace arm is heated to temperatures above the glass transition temperature. FIG. 1 shows that the polymer 20 of the brace arm 5 may be disposed on the side of the second actuator 9 facing the optic body 3, and that the remote side of the second actuator 9 may be free of the polymer 20 of the brace arm 5. It is alternatively conceivable that the polymer 20 of the brace arm 5 completely ensheaths the second actuator 9 that extends within the brace arm 5.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 1 intraocular lens
2 capsular bag
3 optic body
4 haptic element
5 brace arm
6 locking tooth
7 electromagnetic radiation
8 first actuator
9 second actuator
10 bimetal of the first actuator 8
11 bimetal of the second actuator 9
12 first metal
13 second metal
14 thickening of the first actuator 8
15 thickening of the second actuator 9
16 reservoir of the first actuator 8
17 conduit of the first actuator 8
18 substance of the first actuator 8
19 polymer of the haptic element 4
20 polymer of the brace arm 5
21 recess
22 longitudinal brace arm end
23 first flank
24 second flank
25 first longitudinal haptic element end
26 second longitudinal haptic element end
27 optical axis
28 wavelength
29 absorption
30 dimer absorption band
31 monomer absorption band
32 individual absorption band
33 overall absorption
$\lambda_1$ wavelength
$\lambda_2$ wavelength
$\Lambda_1$ first wavelength range
$\Lambda_2$ second wavelength range

What is claimed is:

1. An intraocular lens (IOL) comprising:
an optic body;
a haptic element mounted on the optic body, the haptic element having a haptic curvature and a plurality of recesses on a side of the haptic element facing the optic body;
a first actuator disposed in a region of the optic body and extending alongside the side of the haptic element facing the optic body, the first actuator set up to reversibly change, with a change in a property of the first actuator, the haptic curvature of the haptic element such that the haptic element is moved away from the optic body from a rest position of the haptic element;
a brace arm mounted on the optic body and having a longitudinal brace arm end arranged remote from the optic body, the longitudinal brace arm end being configured to be provided in one of the recesses when the haptic element is in the rest position of the haptic element; and
a second actuator disposed in a region of the optic body and configured to reversibly change, with a change in a property of the second actuator, a brace arm curvature of the brace arm such that the recess in which the longitudinal brace arm end is to be provided can be adjusted with the property of the second actuator.

2. The intraocular lens as claimed in claim 1, wherein the property of the first actuator is a temperature of the first actuator and the first actuator includes a bimetal of the first actuator which extends within the haptic element, and/or
wherein the property of the second actuator is a temperature of the second actuator and the second actuator includes a bimetal of the second actuator which extends within the brace arm.

3. The intraocular lens as claimed in claim 2, wherein the haptic element is in the rest position of the haptic element when the temperature of the first actuator is below a threshold temperature of the first actuator, and
wherein the haptic element is configured to move away from the optic body when the first actuator is heated to temperatures above the threshold temperature of the first actuator.

4. The intraocular lens as claimed in claim 2, wherein the first actuator has a thickening, said thickening having thermally conductive bonding to the bimetal of the first actuator, and/or
wherein the second actuator has a thickening of the second actuator, said thickening of the second actuator having thermally conductive bonding to the bimetal of the second actuator.

5. The intraocular lens as claimed in claim 4, wherein the thickening of the first actuator and/or the thickening of the second actuator is provided in a region of the optic body or in a region adjacent to the optic body.

6. The intraocular lens as claimed in claim 1, wherein the recesses are arranged alongside one another in a direction from a first longitudinal haptic element end of the haptic element to a second longitudinal haptic element end of the haptic element.

7. The intraocular lens as claimed in claim 6, wherein the first longitudinal haptic element end is provided on the optic body and the second longitudinal haptic element end is provided remote from the optic body, or wherein the first longitudinal haptic element end is provided remote from the optic body and the second longitudinal haptic element end is provided on the optic body.

8. The intraocular lens as claimed in claim 6, wherein whichever of the first longitudinal haptic element end and the second longitudinal haptic element end which is provided remote from the optic body, is provided at a different distance away from the optic body depending on the recesses in which the longitudinal brace arm end is arranged.

9. The intraocular lens as claimed in claim 6, wherein the property of the second actuator is a temperature of the second actuator, and
   wherein the longitudinal brace arm end is configured to be provided in one of the recesses in the region of the first longitudinal haptic element end when the temperature of the second actuator is below a threshold temperature of the second actuator, and to move in the direction of the second longitudinal haptic element end when the second actuator is heated to temperatures above the threshold temperature of the second actuator.

10. The intraocular lens as claimed in claim 9, wherein a locking tooth is provided between every two adjacent recesses and has a first flank arranged to face the second longitudinal haptic element end and a second flank arranged to face the first longitudinal haptic element end, and
   wherein the first flank and the second flank are shaped such that, when the haptic element is in its rest position, sliding of the longitudinal brace arm end in the direction of the second longitudinal haptic element end is enabled and sliding of the longitudinal brace arm end toward the first longitudinal haptic element end is prevented.

11. The intraocular lens as claimed in claim 10, wherein the first flank protrudes steeper than the second flank from the surface of the haptic element.

12. The intraocular lens as claimed in claim 1, wherein a locking tooth is disposed between every two adjacent recesses.

13. The intraocular lens as claimed in claim 1, wherein the haptic element includes a polymer which comes into contact with the first actuator, and/or
   wherein the brace arm includes a polymer which comes into contact with the second actuator.

14. The intraocular lens as claimed in claim 1, wherein the intraocular lens has two of the haptic elements, one of the first actuators and one of the brace arms for each of the haptic elements, and one of the second actuators for each brace arm.

* * * * *